(12) United States Patent
Brown et al.

(10) Patent No.: US 8,034,631 B2
(45) Date of Patent: *Oct. 11, 2011

(54) SYSTEMS FOR HOMOGENEOUS IMMUNOASSAYS FOR MULTIPLE ALLERGENS

(75) Inventors: Christopher R. Brown, San Mateo, CA (US); James T. Murai, San Bruno, CA (US)

(73) Assignee: ImmuneTech, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/006,392

(22) Filed: Jan. 13, 2011

(65) Prior Publication Data

US 2011/0110828 A1     May 12, 2011

Related U.S. Application Data

(63) Continuation of application No. 12/316,838, filed on Dec. 16, 2008, now Pat. No. 7,892,853, which is a continuation of application No. 11/786,193, filed on Apr. 10, 2007, now Pat. No. 7,491,553, which is a continuation of application No. 10/387,790, filed on Mar. 12, 2003, now abandoned, which is a continuation-in-part of application No. 10/006,483, filed on Dec. 6, 2001, now abandoned.

(51) Int. Cl.
    *G01N 33/543* (2006.01)
(52) U.S. Cl. ........ 436/523; 435/7.1; 435/7.92; 435/7.93; 435/7.94; 436/164; 436/172; 436/518
(58) Field of Classification Search .................. None
    See application file for complete search history.

(56) References Cited

U.S. PATENT DOCUMENTS

| | | | |
|---|---|---|---|
| 4,228,237 A | 10/1980 | Hevey et al. | |
| 4,279,617 A | 7/1981 | Masson et al. | |
| 4,459,360 A | 7/1984 | Marinkovich | |
| 4,520,110 A | 5/1985 | Stryer et al. | |
| 4,743,541 A | 5/1988 | Higgins et al. | |
| 5,028,545 A | 7/1991 | Soini | |
| 5,082,768 A | 1/1992 | Burd et al. | |
| 5,362,655 A | 11/1994 | Schenk et al. | |
| 5,478,926 A | 12/1995 | Nishimura et al. | |
| 5,494,830 A | 2/1996 | Hubscher | |
| 5,512,659 A | 4/1996 | Ullman et al. | |
| 5,656,207 A | 8/1997 | Woodhead et al. | |
| 5,846,703 A | 12/1998 | Devlin et al. | |
| 5,866,321 A | 2/1999 | Matsue et al. | |
| 5,972,630 A | 10/1999 | Cromer et al. | |
| 5,981,180 A | 11/1999 | Chandler et al. | |
| 6,054,303 A | 4/2000 | Davalian et al. | |
| 6,087,188 A | 7/2000 | Johansen et al. | |
| 6,159,748 A | 12/2000 | Hechinger | |
| 6,184,042 B1 | 2/2001 | Neumann et al. | |
| 6,218,134 B1 | 4/2001 | Yamauchi et al. | |
| 6,245,513 B1 | 6/2001 | Lane et al. | |
| 6,264,619 B1 | 7/2001 | Ferguson | |
| 6,268,222 B1 | 7/2001 | Chandler et al. | |
| 6,274,325 B1 | 8/2001 | Deger et al. | |
| 6,406,667 B1 | 6/2002 | Singh et al. | |
| 6,449,562 B1 | 9/2002 | Chandler et al. | |
| 6,524,793 B1 | 2/2003 | Chandler et al. | |
| 6,645,732 B2 | 11/2003 | Faatz et al. | |
| 6,939,720 B2 | 9/2005 | Chandler et al. | |
| 6,979,567 B2 | 12/2005 | Herron et al. | |
| 7,465,540 B2 | 12/2008 | Jacobson et al. | |
| 7,491,553 B2 * | 2/2009 | Brown et al. | 436/523 |
| 7,674,632 B1 | 3/2010 | Connelly et al. | |
| 7,892,853 B2 * | 2/2011 | Brown et al. | 436/523 |
| 2002/0004199 A1 * | 1/2002 | Hechinger | 435/5 |
| 2002/0045195 A1 | 4/2002 | Hubscher et al. | |
| 2002/0055176 A1 | 5/2002 | Ray | |
| 2002/0119497 A1 | 8/2002 | Wild et al. | |
| 2003/0054356 A1 | 3/2003 | Jacobson et al. | |
| 2003/0096433 A1 | 5/2003 | Meyer-Almes | |
| 2005/0101031 A1 | 5/2005 | Hiller et al. | |
| 2005/0191647 A1 | 9/2005 | Meyer-Almes | |
| 2006/0246506 A1 | 11/2006 | Pulli et al. | |
| 2009/0137060 A1 | 5/2009 | Lund-Johansen | |

FOREIGN PATENT DOCUMENTS

| | | |
|---|---|---|
| DK | 0585369 | 4/1999 |
| EP | 0 556 745 | 12/1993 |
| EP | 0 700 514 | 11/2001 |
| EP | 1 195 606 | 4/2002 |
| ES | 2 251 722 | 5/2006 |
| GB | 2459384 | 10/2009 |
| IT | 1235349 | 6/1992 |
| NL | 1026678 | 1/2006 |

(Continued)

OTHER PUBLICATIONS

Barbarakis, M.S., et al., Enhancement of the Emission Intensity of Fluorophore-Labeled Avidin by Biotin and Biotin Dervatives. Evaluation of Different Fluorophores for Improved Sensitvity, *Talanta*, Jul. 1993, 40(7), pp. 1139-1145.

(Continued)

*Primary Examiner* — Melanie J Yu
*Assistant Examiner* — Gary W Counts
(74) *Attorney, Agent, or Firm* — Syndicated Law; Brian S. Boyer

(57) ABSTRACT

A homogeneous immunoassay method and system for quantitative determination of total immunoglobulin E and specific antibody levels to a plurality of allergens, in which a relatively small sampling of blood is required. The method utilizes relatively small microparticles in aqueous suspension. The immunoassay procedure is an immunometric sandwich procedure preferably utilizing biotin-streptavidin signal amplification techniques and R-phycoerytherin fluorescent labels.

25 Claims, 4 Drawing Sheets

FOREIGN PATENT DOCUMENTS

| | | |
|---|---|---|
| SE | 504798 | 4/1997 |
| WO | WO 97/14028 | 4/1997 |
| WO | WO 99/36564 | 7/1999 |
| WO | WO 00/50172 | 8/2000 |
| WO | WO 03/050539 | 6/2003 |
| WO | WO 2004/046733 | 6/2004 |
| WO | WO 2007/008084 | 1/2007 |
| WO | WO 2007/067680 | 6/2007 |
| WO | WO 2009/048530 | 4/2009 |

OTHER PUBLICATIONS

Bishop, J.E., et al., A Flow Cyometric Immunoassay for beta2-microglobulin in Whole Blood, *Journal of Immunological Methods*, 210(1), Dec. 15, 1997, pp. 79-87.

Carpenter, A.B., Enzyme-Linked Immunoassays, Chapter 2, *Manual of Clinical Laboratory Immunology*, 4$^{th}$ Edition, 1992, Rose et al. eds., American Society for Microbiology, Washington D.C., pp. 2-6.

Carson, R.T., et al., Simultaneous Quantitation of 15 Cytokines Using a Multiplexed Flow Cytometric Assay, *Journal of Immunological Methods*, Jul. 30, 1999, 227(1-2), pp. 41-52.

Dafforn, A., et al., Miniaturization of the Luminescent Oxygen Channeling Immunoassay (LOCI(TM)) for use in Multiplex Array Formats and Other Biochips, *Clinical Chemistry*, Sep. 2000, 46(9), pp. 1495-1497.

Derer, M.M., et al., Application of the Dot Immunobinding Assay to Allergy Diagnosis, *Journal of Allergy and Clinical Immunology*, 74(1), Jul. 1984, pp. 85-92.

Diamandis, et al., Immunoassay, Academic Press, Chapter 11, The Avidin-Biotin System, 1996, pp. 237-267.

Fulton, R.J., et al., Advanced Multiplexed Analysis with the FlowMetrix™ System, *Clinical Chemistry*, vol. 43, No. 9, 1997, pp. 1749-1756.

Fulwyler, M.J., et al., Flow Microsphere Immunoassay for the Quantitative and Simultaneous Detection of Multiple Soluble Analytes, *Methods in Cell Biology*, 1990, 33, pp. 613-629.

Haugland, R.P., et al., Preparation of Avidin Conjugates, Chapter 18, Immunochemical Protocols, 2$^{nd}$ Edition, 1998, J.D. Pound ed. Humana Press Inc., Totowa, N.J., pp. 185-196.

Hlavacek, W.S., et al., Quantifying Aggregation of IgE-FcεRI by Multivalent Antigen, *Biophysical Journal*, vol. 76, May 1999, pp. 2421-2431.

Johansson, S.G.O., et al., In Vitro Assays for Immunoglobin E, *Clinical Reviews in Allergy*, vol. 6, 1988, pp. 93-139.

Luminex, Allergy Testing: Rapid Economical, Multi-Analyte, *Luminex Technical Bulletin*, 2 pages, Rev. HI109, Jun. 13, 2003.

Luminex, The Luminex LabMap System, *Luminex Technical Bulletin*, 3 pages, Rev. AL010, Jun. 13, 2003.

Nakamura, A.B., et al., Fluorescence Immunoassays, Chapter 3, *Manual of Clinical Laboratory Immunology*, 4$^{th}$ Edition, 1992, N.R. Rose et al. eds. American Society for Microbiology, Washington D.C., pp. 7-15.

Olivieri, V., et al., Capture Assay for Specific IgE: An Improved Quantitative Method, *Journal of Immunological Methods*, 157(1-2), Jan. 4, 1993, pp. 65-72.

Park, M.K, et al., A Latex Bead-Based Flow Cytometric Immunoassay Capable of Simultaneous Typing of Multiple Pneumococcal Serotypes (Multibead Assay), Clinical and Diagnostic Laboratory Immunology, May 2000, 7(3), pp. 486-489.

Schulz, A. et al., Detection of Target Molecules on the Single Molecule Level Using Confocal Fluorescence Microscopy in Combination with Microelectophoresis, Conference: Trends in Optics and Photonics, Laser Application to Chemical and Environmental Analysis, Santa Fe, NM, Feb. 11-13, 2000, pp. xiii+213.

Swartzman, E.E., et al., A Homogeneous and Multiplexed Immunoassay for High-Throughput Screening Using Fluorometric Microvolume Assay Technology, *Analytical Biochemistry*, 271(2), Jul. 1, 1999, pp. 143-151.

Ullman, E.F., Homogeneous Immunoassays: Historical Perspective and Future Promise, *Journal of Chemical Education*, 76(6), 1999, p. 781.

Wild, et al., The Immunoassay Handbook, Signal Generation and Detection Systems, M. Stockton Press, New York, 1994, pp. 54, 63-82.

Xu, J.X., et al., A Method, Distribution-Analyzing Latex Immunoassay (DALIA), to Measure Specific Immunoglobulin G Against Mite and Wheat Allergen in Human Sera, *Allergy*, May. 1994, 49(5), pp. 323-329.

Anonymous, FluoroTable: Common Fluorophores, 6 pages, 2001 [online] URL: http://web.archive.org/web/20011203181756/http://info.med.yale.edu/genetics/ward/tavi/FISHdyes2.tml.

\* cited by examiner

Allergic Individuals

| Allergen | IU/mL | Class | Allergen | IU/mL | Class | Allergen | IU/mL | Class |
|---|---|---|---|---|---|---|---|---|
| Bermuda Grass | 3.21 | 2 | Bermuda Grass | 5.12 | 3 | Bermuda Grass | 43.16 | 4 |
| Cedar | 2.90 | 2 | Cedar | 5.21 | 3 | Cedar | 83.06 | 5 |
| Ragweed | 17.49 | 3 | Ragweed | 7.05 | 3 | Ragweed | 30.13 | 4 |
| Timothy Grass | 15.18 | 3 | Timothy Grass | 36.80 | 4 | Timothy Grass | >100 | 6 |
| Cat | 13.84 | 3 | Cat | 5.32 | 3 | Cat | 20.12 | 4 |
| Housedust Mite | 59.60 | 5 | Housedust Mite | 18.05 | 4 | Housedust Mite | <0.35 | 0 |
| Alternaria (Mold) | 5.45 | 3 | Alternaria (Mold) | 1.55 | 2 | Alternaria (Mold) | <0.35 | 0 |
| Egg White | <0.35 | 0 | Egg White | 5.06 | 3 | Egg White | <0.35 | 0 |
| Milk | <0.35 | 0 | Milk | 4.63 | 3 | Milk | <0.35 | 0 |
| Wheat | 0.50 | 1 | Wheat | 3.44 | 2 | Wheat | 20.32 | 4 |

FIG. 1 (cont.)

Non-Allergic Individuals

| Allergen | IU/mL | Class | Allergen | IU/mL | Class |
|---|---|---|---|---|---|
| Bermuda Grass | <0.35 | 0 | Bermuda Grass | <0.35 | 0 |
| Cedar | <0.35 | 0 | Cedar | <0.35 | 0 |
| Ragweed | <0.35 | 0 | Ragweed | <0.35 | 0 |
| Timothy Grass | <0.35 | 0 | Timothy Grass | <0.35 | 0 |
| Cat | <0.35 | 0 | Cat | <0.35 | 0 |
| Housedust Mite | <0.35 | 0 | Housedust Mite | <0.35 | 0 |
| Alternaria (Mold) | <0.35 | 0 | Alternaria (Mold) | <0.35 | 0 |
| Egg White | <0.35 | 0 | Egg White | <0.35 | 0 |
| Milk | <0.35 | 0 | Milk | <0.35 | 0 |
| Wheat | <0.35 | 0 | Wheat | <0.35 | 0 |

Interpretation of Results

| Allergen-Specific IgE Concentration IU/mL | Class | Interpretation |
|---|---|---|
| <0.35 | 0 | Negative |
| 0.35 - 0.69 | 1 | Low Positive |
| 0.70 - 3.49 | 2 | Moderate Positive |
| 3.50 - 17.49 | 3 | Moderate to High |
| 17.50 - 49.99 | 4 | High Positive |
| 50.00 - 100 | 5 | Very High Positive |
| >100 | 6 | Extremely High |

FIG. 1 (cont.)

SYSTEMS FOR HOMOGENEOUS IMMUNOASSAYS FOR MULTIPLE ALLERGENS

CROSS-REFERENCE TO RELATED APPLICATIONS

This application is a continuation of U.S. application Ser. No. 12/316,838, filed Dec. 16, 2008, now U.S. Pat. No. 7,892,853, which is a continuation of U.S. application Ser. No. 11/786,193, filed Apr. 10, 2007, now U.S. Pat. No. 7,491,553, which is a continuation of U.S. application Ser. No. 10/387,790, filed Mar. 12, 2003, now abandoned, which is a continuation-in-part of U.S. application Ser. No. 10/006,483, filed Dec. 6, 2001, now abandoned; and, each of these applications is incorporated herein in its entirety by reference.

BACKGROUND OF THE INVENTION

1. Field of the Invention

This invention relates to a homogenous immunoassay method and a system for determining specific antibody levels to a multiplicity of allergens from a blood sample, or for determining total immunoglobulins E levels in such a sample, for the purpose of diagnosing allergy.

2. Background and Prior Art

"Allergy" is synonymous with atopy or hypersensitivity and is the result of an immunologically mediated reaction by individuals to various antigenic materials, known as allergens. People with allergies produce allergen-specific immunoglobulins, IgE and IgG, in response to exposure to normally harmless substances from pollens, molds, dander or foods, which are inhaled or ingested. The generated antibodies are released to circulate in the blood and eventually fix to specific cells in tissue. Exposure to allergens generally results in immediate or delayed reactions, manifested in a number of commonly identifiable symptoms, such as sneezing, itchy eyes, runny nose and inflammation of the lungs and nasal passages. The term "allergy" is also generally synonymous with hay fever, rhinitis, eczema, hives, and linked to the onset of asthma. The diagnosis of allergy involves a review of the patient history, physical examinations and running a confirmatory diagnostic test to identify whether the patient's symptoms are of allergic or non-allergic origin. If allergy is responsible for the symptoms, then the allergens responsible must be identified. Patients with atopic or allergic diseases may be mono-sensitive to one allergen; however, sensitization to multiple allergens is more usual. Reactions of persons to allergens can range from the annoying to the severe or even fatal. It therefore is desirable to be able to determine not only whether a person has allergies, but if so, to what allergens and to what level of severity, so that exposure can be avoided, minimized or mitigated through pharmacotherapeutic or immunotherapeutic methods Confirmatory diagnostic testing may be conducted by in-vivo skin testing, in-vivo provocation testing, or in-vitro testing for the presence of circulating allergen-specific antibodies from blood samples. Direct provocation, by direct inhalation or ingestion of possible offending allergens, while relevant, is unpleasant, possibly dangerous and cannot be performed for multiple allergens at one sitting.

Skin testing (also referred to as skin prick testing or scratch testing) is an in vivo procedure that involves applying an allergen sample, or more generally a multiplicity of allergens, directly to a patient's forearm or back via a small needle scratch and measuring the size of the inflammatory reaction (wheal) at the applied site on the skin. Skin prick testing is widely used, is reliable under optimal testing conditions, can be painful, is subject to large differences in technique and interpretations, and cannot be used on patients taking certain drugs or patients with skin problems. Furthermore, both provocation and skin prick in-vivo diagnostic methods have the potential for sensitizing patients to new allergens and, in extreme cases, eliciting a life-threatening anaphylactic reaction upon direct exposure to the offending allergen(s).

In vitro diagnostic testing methods directly measure circulating levels of allergen-specific antibodies in a sample of blood obtained from patients. These methods are generally immunoassay procedures that are reproducible, are equivalent in sensitivity and specificity to well conducted skin prick tests, are unaffected by any of the factors which prevent the use of either of the two in vivo methods, and do not cause anaphylactic events. Immunoassay techniques capable of measuring specific antibody levels to single allergens have been employed for many years (Johansson, S. G. O. and Yman, L., In vitro assay for immunoglobulin E, Coin. Rev. Allergy 6, 93-139, 1988). Alternatively, methods that measure allergen-specific levels to a plurality of allergens simultaneously have provided more useful screenings of allergy as, for example, described in U.S. Pat. Nos. 4,459,360 and 5,082,768. U.S. Pat. No. 6,087,188 describes a method of detecting an antibody in a sample using paramagnetic particles and a chemiluminescent acridinium compound bound to avidin or streptavidin. The method described in this patent is stated to be useful for the detection of allergens. However, the method is limited to detection of a single allergen in a given sample.

In the field of clinical diagnostics there is a broad category of methods available for determining an expanding list of clinically relevant analytes. One such category is immunoassays, which are currently used to determine the presence or concentration of various analytes in biological samples, both conveniently and reliably (The Immunoassay Handbook, edited by David Wild, M Stockton Press, 1994). Immunoassays utilize specific binding agents to target analytes in fluids, where at least one such binding agent is generally labeled with a variety of compounds, including radioisotopes, enzymes and fluorescent or chemiluminescent compounds, that can be measured by radioactive disintegrations, enzymatic induced color-producing substrates, fluorescent output or inhibition and chemiluminescent light output. Such specific binding agents typically include analyte specific antibodies (immunoglobulins) and antibody fragments, receptors, lectins, and genetically or chemically engineered artificial antibodies. Notable immunoassay methods include, for example, radioimmunoassay (RIA), enzyme-linked immunosorbent assay (ELIZA) (Enzyme-Immunoassay, Edward T. Maggio, CRC Press, 1980), fluorescent immunoassay (FIA) and chemiluminescent assays (CLA) (Luminescent Assays, Perspectives in Endocrinology and Clinical Chemistry, Vol. 1, Mario Serio and Mario Pazzagli, Raven Press, 1982), (Bioluminescence and Chemiluminescense, Basic Chemistry and Analytical Applications, Marlene, A. DeLuca and William D. McElroy, Academic Press, 1981), (Journal of Bioluminescence, Vol. 4, M. Pazzagli, et al., Proceedings of the Vth International Symposium on Bioluminescence and Chemiluminescence, Wiley, 1989), etc. Numerous method variations and devices for performing such assays are available, are known to those familiar with the art, and can be found in the scientific and patent literature.

Immunoassays may be heterogeneous or homogeneous. Heterogeneous immunoassays have been applied to both small and large molecular weight analytes and require separation of bound materials (to be detected or determined) from free materials (which may interfere with that determination).

Heterogeneous immunoassays may comprise an antibody or an antigen immobilized on solid surfaces such as plastic microtiter plates, beads, tubes, or the like or on membrane sheets, chips and pieces of glass, nylon, cellulose or the like (Immobilized Enzymes, Antigens, Antibodies, and Peptides, Howard H. Weetall, Marcel Dekker, Inc., 1975). In heterogeneous immunoassays, antigen-antibody complexes bound to the solid phase are separated from unreacted and non-specific analyte in solution, generally by centrifugation, filtration, precipitation, magnetic separation or aspiration of fluids from solid phases, followed by repeated washing of the solid phase bound antigen-antibody complex. Of particular interest are immunometric "sandwich" assays (Immunochemistry of Solid-Phase Immunoassay, John E. Butler, CRC Press, 1991) which first require binding of an immobilized antigen or antibody with the target analyte from the biological sample. Separation of the immobilized pair and subsequent repeated washing is followed by the introduction of a secondary binding agent specific to the analyte, said secondary binding agents usually being chemically conjugated with radioisotopes, enzyme, fluorescent or chemiluminescent labels described earlier. Secondary binding agents are typically immunoglobulin antibodies, antibody fragments, monoclonal antibodies or recombinant antibodies. The analyte is "sandwiched" between the first immobilized antigen or antibody and the labeled secondary binding agent. A subsequent separation and washing is required to remove unbound labeled secondary binding agents. Direct measurement of the labeled, immobilized bound complex or indirect measurement with the use of substrates is then undertaken. It can be appreciated by those familiar with the art of conducting solid phase immunoassays that the procedures are laborious, time consuming and require special equipment or devices for separating immobilized binding agents and analytes.

Homogeneous assays are, in general, liquid phase procedures that do not utilize antigens or antibodies that are immobilized on solid materials. Separation and washing steps are not required. The procedures are more commonly involved with the use of fluorescently-labeled antigens or antibodies which upon binding with a target analyte undergo an excitation or quenching of fluorescence emissions, due to the close steric proximity of the binding pair. Homogeneous methods have typically been developed for the detection of haptens, small molecules, such as drugs, hormones and peptides. Macromolecule analytes, such as proteins or peptides with greater than 5000 molecular weight, usually are not determined by homogeneous methods due to a lack of assay sensitivities. A homogeneous method for detection of proteins was reported in U.S. Pat. No. 5,807,675 which required chemical modifications to both binding agents, but is limited to the detection of single analytes.

For the diagnosis of allergy determination of total immunoglobulin E levels is helpful, but more importantly there is a need for a convenient and reliable immunoassay method that simultaneously measures specific immunoglobulin antibody levels to a panel of allergens, where one or more allergens may be responsible for the onset of allergic symptoms. It is further desired that the immunoassay protocol assay be easily carried out and adaptable to automation. In vitro methods currently available utilize heterogeneous immunoassay methods where separation and washing is required, making them labor-intensive, time-intensive and difficult to automate. It also would be advantageous to combine the versatility and sensitivity of solid phase heterogeneous assay methods with the ease of a homogeneous protocol. Furthermore, conducting in vitro allergy tests on a panel of allergens requires drawing a significant sample, generally 3-5 milliliters, of venous blood from the patient. Indeed, the patient must visit a laboratory or physician's office for the single purpose of having the blood sample drawn.

Recent advances in immunoassay methods have introduced microtechniques that utilize smaller solid phases and smaller sample requirements. One example is a microimmunoassay method for conducting analysis and detection of multiple biomolecules that is described in U.S. Pat. No. 5,981,180. Apparatus of this general type has been marketed by the Luminex Corporation under the trademark FLOWMETRIX. The technology incorporates a flow cytometric procedure and the use of small, 5.6 micrometer polystyrene bead sets, each set containing an internal fluorescent signature, that enables detection of multiple analytes. For in vitro allergy testing, where specific levels of antibody are in low concentrations in circulating blood, undiluted blood or serum is required to enable the detection of antibodies that are at sub-nanogram- to picogram-per-milliliter levels. Up to now, heterogeneous rather than homogeneous immunoassay methods have been employed with existing in-vitro allergy testing methods, since undiluted blood or serum very often contains microgram levels of free or non-specific (total) antibody levels which can interfere with determinations using homogeneous assays.

Homogeneous assay methods using undiluted blood or serum to measure sub-nanogram- or picogram-per-milliliter levels of antibody have been known to show falsely low or falsely undetectable levels of specific antibodies in samples where the free or non-specific antibody levels in undiluted serum are in the microgram per milliliter range. Such false results are known as a "hook effect". The hook effect is described by Robard, D., (Radioisotopes: 37, (10), 1988), in the Immunoassay Handbook (Edited by David Wild, M Stockton Press 1994) and the Manual of Clinical Laboratory Immunology (4th ed., Rose, et al., Editors) published by the American Society for Microbiology (Chapter 2, page 5). It involves an unexpected fall in the amount of an analyte at the high end of a dose-response curve, which results in a gross underestimation of the analyte. The hook effect is caused by high concentrations of free, i.e., unbound, analyte from neat serum or blood samples that bind to secondary binding agents, depleting the availability of the secondary binding agent to the solid phase bound analyte, subsequently rendering a falsely lower signal, hence indicating a falsely low analyte concentration. Heterogeneous assay formats, specifically, immunometric sandwich assays, generally circumvent the interference with the separation and washing steps inherent to the procedures.

The above-mentioned references suggest several ways that laboratories can deal with this hook effect. One suggested strategy is to run all patient samples at two dilutions as a screen for this problem. If the more dilute sample indicates a significantly higher level of analyte, the laboratory is alerted to the possibility of a hook effect. Various dilutions can then be carried out to provide an accurate determination of the existing amount of analyte in the sample. Such procedures, of course, result in duplication of work and lengthening of the time and costs required to conduct testing of the sample from a given patient. Alternatively, large excesses of secondary binding agent, sufficient to bind both bound and unbound specific and non-specific analyte antibody can be used. However, this approach has not proved practical due to the large concentrations of unbound specific and non-specific analyte antibody in undiluted blood, the relatively large serum or plasma volumes typically required in conducting in-vitro allergy tests, and the costs for secondary binding agent that would be used.

It would be advantageous to provide a homogeneous assay method for detecting the presence of specific antibodies to a multiplicity of allergens, simultaneously in a single test, or determining the total IgE antibody content in a blood sample, that would not be prone to the occurrence of the hook effect. It also would be advantageous to provide a method of testing blood samples from a patient for allergies that could eliminate the requirement that the patient visit a laboratory or physician's office, as well as the need to have a fairly substantial amount of blood drawn for the purpose of this test. The invention described herein provides such advantages, as well as others that may be apparent from the information described.

SUMMARY OF THE INVENTION

Speaking very generally, this invention provides a method and a system for simultaneously detecting and quantifying levels of specific immunoglobulin antibodies to a plurality of allergens, using a very small sampling of blood, for the purpose of diagnosing allergy. The invention also provides a method and a system for detecting and quantifying levels of total immunoglobulin E in such a small blood sampling.

In general, the method of this invention comprises simultaneously measuring specific immunoglobin antibody levels to from 2 to about 100 allergens in a blood sample, said method comprising:
(a) collecting a blood sample of from about 10 to about 100 μL from an individual;
(b) performing a homogeneous immunoassay on the blood sample or a portion thereof, wherein the immunoassay is capable of determining specific immunoglobin antibody levels to from 2 to about 100 allergens; and
(c) determining the said specific immunoglobin antibody levels,
and the system comprises a system for simultaneously measuring a plurality of specific immunoglobin antibody levels by use of a homogeneous immunoassay, said system comprising:
(a) a plurality of particles coupled to from 2 to about 100 allergens;
(b) a first conjugate comprising an anti-human IgE or IgG antibody conjugated to a first member of a specific binding pair; and
(c) a second conjugate comprising a second specific binding pair member that binds to the first specific binding pair member; the system being capable of conducting simultaneous quantitative determination of specific immunoglobin antibody levels to from 2 to about 100 allergens, by a homogeneous immunoassay.

The system and method thus enable, for the first time, the conducting of simultaneous determinations of a plurality (from 2 to about 100) of allergens on a relatively small sample of blood.

One preferred method comprises a homogeneous immunoassay for simultaneously detecting and quantifying specific immunoglobulin antibodies to a plurality of allergens in a blood sample, comprising:
(a) contacting a blood sample having a volume of from about 1 to about 25 μL, preferably 1-10 μL, more preferably 1-5 μL, with a plurality of particles coupled to a plurality of allergens, the particles being in suspension in from about 1 to about 50 μL, preferably from about 1 to about 10 μL, of an aqueous medium, each combination of particles with a specific allergen being distinguishable from combinations of the particles with other allergens, under conditions whereby allergen-specific immunoglobulin antibodies present in the blood sample bind specifically to one or more of the allergens that are coupled to the particles;
(b) thereafter contacting the materials from step (a) with a first conjugate comprising an anti-human IgE or IgG antibody conjugated to a first member of a specific binding pair, said specific binding pair having the capability of amplifying fluorescent signal output, under conditions whereby the anti-human antibody binds to the immunoglobulin antibodies;
(c) thereafter contacting the materials from step (b) with a second conjugate containing a fluorophore moiety coupled to a second member of the specific binding pair under conditions whereby the second member of the specific binding pair binds to the first member of the pair; and
(d) thereafter measuring the fluorescence emitted by the products of step (c).

A second method comprises a homogeneous immunoassay for detecting and quantifying total immunoglobulin E levels in a blood sample, comprising:
(a) contacting a blood sample having a volume of from about 0.5 to about 10 μL, preferably from about 1 to about 5 μL, more preferably from about 1 to about 2 μL, with a plurality of particles coupled to anti-human immunoglobulin E, the particles being in suspension in from about 1 to about 50 μL of an aqueous medium;
(b) thereafter contacting the materials from step (a) with a first conjugate comprising an anti-human IgE antibody conjugated to a first member of a specific binding pair, said specific binding pair having the capability of amplifying fluorescent signal output, under conditions whereby the anti-human antibody binds to the anti-human immunoglobulin E;
(c) thereafter contacting the materials from step (b) with a second conjugate containing a fluorophore moiety coupled to a second member of the specific binding pair under conditions whereby the second member of the specific binding pair binds to the first member of the pair; and
(d) thereafter measuring the fluorescence emitted by products of step (c).

Similarly, one system of this invention comprises a system for quantitative determination of specific immunoglobulin (IgE or IgG) antibody levels to allergens in a blood sample comprising:
(a) a plurality of particles coupled to a plurality of allergens, the particles being in suspension in from about 1 to about 50 μL of an aqueous medium, each combination of particles with a specific allergen being distinguishable from combinations of the particles with other allergens;
(b) a first conjugate comprising an anti-human IgE or IgG antibody conjugated to a first member of a specific binding pair, said specific binding pair having the capability of amplifying fluorescent signal output, the first conjugate having from 10 to 30 molecules, preferably 15 to 25 molecules, of the first binding pair member conjugated to one molecule of the anti-human antibody;
(c) a second conjugate comprising a second member that binds specifically to the first member of the specific binding pair, the second member being coupled to a fluorophore moiety;
(d) the mole ratio of first conjugate to the second conjugate being from about 1:1 to about 1:5, preferably from about 1:1 to about 1:2.

The invention further comprises a system for quantitative determination of total immunoglobulin E levels in a blood sample comprising:

(a) a plurality of particles coupled to anti-human IgE antibody, the particles being in suspension in from about 1 to about 50 μL of an aqueous medium;

(b) a first conjugate comprising an anti-human IgE or IgG antibody conjugated to a first member of a specific binding pair, said specific binding pair having the capability of amplifying fluorescent signal output, the first conjugate having from 10 to 30 molecules, preferably 15 to 25 molecules, of the first binding pair member conjugated to one molecule of the anti-human antibody;

(c) a second conjugate comprising a phycobiliprotein and a second specific binding pair member that binds specifically to the first specific binding pair member;

(d) the mole ratio of the first conjugate to the second conjugate being from about 1:1 to about 1:5, preferably from about 1:1 to about 1:2.

DETAILED DESCRIPTION OF THE INVENTION

Figure 1:
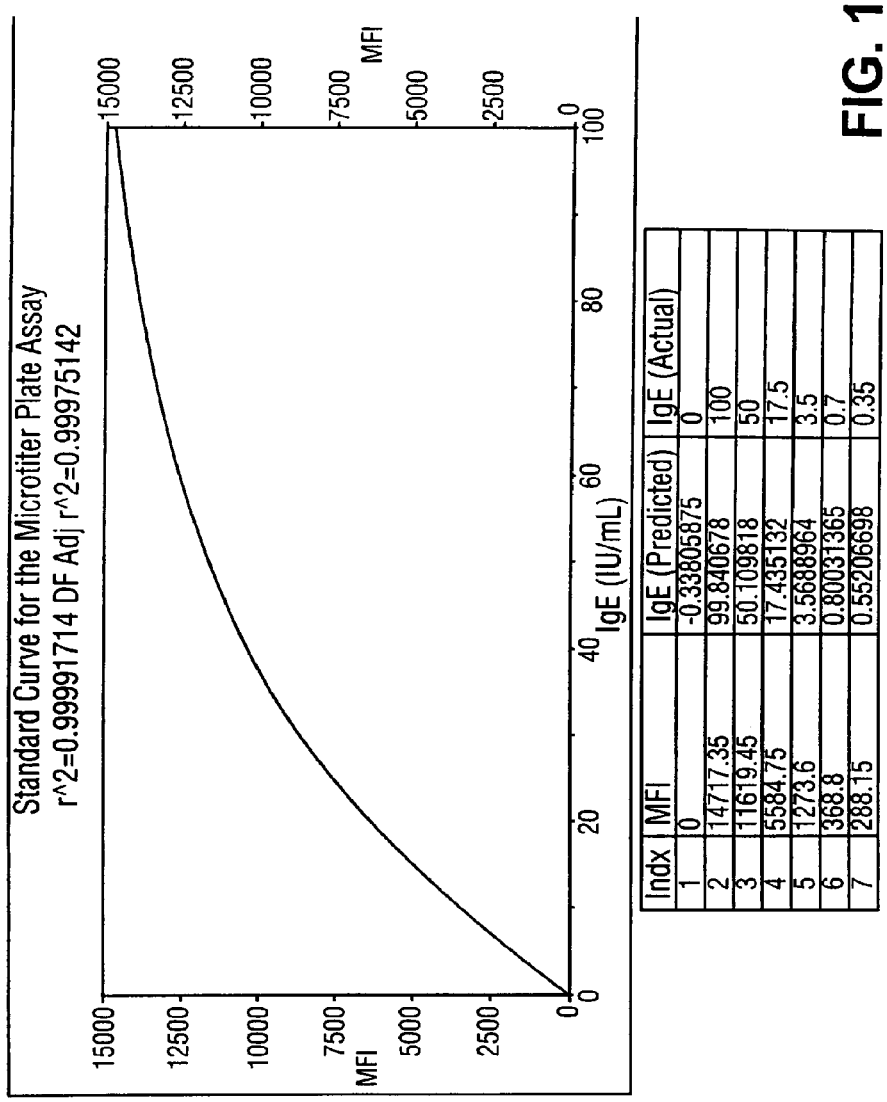
FIG. 1 is a tabulated and graphical view of a specific IgE assay against a panel of ten allergens according to the present invention in accordance with Example 1

This invention provides a method and a system for detecting and quantifying specific antibodies to allergens in a blood sample of an individual, for the diagnosis of allergy. Heretofore, in vitro tests for allergy have employed immunoassay methods requiring venous draw samplings of blood to enable testing on a panel of allergens. Typically, sample requirements of current methods, to determine levels of specific antibodies against a panel of five or more allergens, are from one to three milliliters of blood. As compared to the prior art, the invention limits the sample volume requirements to ten microliters of sample or less, which can be used to test against two or more allergens, preferably against ten, twenty, forty or more allergens. The amount of sample required is sufficiently small that individuals can remotely obtain a blood sample using a fingerstick or similar procedure. The invention removes the need for obtaining blood samples by venous drawing procedures at physicians' offices, hospital laboratories or clinical reference laboratories.

In a preferred embodiment of this invention, the individual whose blood is to be tested is provided with a kit for collecting and mailing, or otherwise submitting, the blood sample. The kit typically contains one or more devices for puncturing the skin of a finger or other portion of the body (e.g., a "fingerprick" or "fingerstick" device) in order to draw some blood, an alcohol or other antiseptic swab for cleaning the area to be punctured, a vial or other small container in which the blood is to be put and sealed, and an appropriate container for mailing the blood sample to the laboratory for testing. The kit also may contain additional items such as adhesives to protect the wound, instructional inserts and labels with individual identification numbers (e.g., PIN) for samples. In any case, the exact form and contents of such a kit can vary according to the desires of the laboratory and do not form a part of this invention. Numerous components for such kits are readily available for collection and/or testing of blood (for instance, at home) for various purposes.

In addition, it should be noted that the providing of a blood sample by the individual without visiting a physician's office or laboratory is not a limiting feature of this invention, but only an advantage of it. The blood sample can well be taken during a visit to a physician's office, and submitted to a laboratory for testing. In such a case, other advantages of the invention, such as the ability to test a small sample without requiring dilution and/or duplication of tests, are achieved.

The use of such a limited sample volume essentially avoids the presence of large amounts of free IgE antibody in the assay and the resulting hook effects that have heretofore been a barrier to homogeneous formats with in vitro tests for allergy. In vitro testing methods for diagnosing allergy have heretofore employed heterogenous immunoassay methods, more generally, two-site immunometric sandwich assay procedures that require separation and washing steps to be performed. Neat serum, plasma or blood samples are also necessary in these procedures to attain the levels of sensitivity required to determine blood circulating levels of specific antibody that are in the $10^{-9}$ to $10^{-12}$ molar levels or in low nanogram/mL to picogram/mL range. Up till now homogeneous assays have not been employed, due to high levels of specific and nonspecific antibody that are generally present in neat samples of blood from allergic individuals, and the occurrence of the high-dose hook effect in these assays. The invention provides an assay method that combines a solid phase sandwich immunoassay procedure with a homogeneous assay format, where there is no requirement for separation of materials, washing, etc., and no requirement for sample dilution.

The assay method quantitates levels of total IgE and specific antibody levels that are essential to allergy diagnosis and to the degree or severity of allergic response to known allergens.

A preliminary step in carrying out the method and assembling the system for use in this invention is the preparation and collection of a plurality of solid particles coupled to a plurality of allergens so as to provide a panel of allergens to be tested, for instance, to determine whether an individual's allergic symptoms are mediated by one or more of the allergens under investigation.

Each combination of particles with a specific allergen in the panel is distinguishable from combinations of particles with other allergens. A specific allergen can be comprised of extracted proteins, protein fractions purified by chromatographic or affinity chromatographic methods, recombinant proteins or combinations of the above. Allergen mixes, such as two or more grasses, trees or foods, for example, can also be utilized. The capability to distinguish between combinations of particles with different allergens is accomplished by providing a plurality of particles of different types. That is, the particles may be divided into subsets, with each subset being distinguishable from other subsets according to a particular property, characteristic or characteristics. For example, the particles may be divided into subsets where each subset is capable of being distinguished by a specific color or emission spectra, which may be provided by the presence of a fluorochrome or combinations of fluorochromes incorporated within or on it, for example, as described in U.S. Pat. No. 5,981,180. Each subset of the particles is coupled to a specific allergen so that, again, the combination of particles with specific allergen is distinguishable from combinations of particles with other allergens, in accordance with the particular characteristic or characteristics that distinguishes the particle or bead in question from others that are used. The coupling of the allergens to the beads or particles is accomplished by covalent coupling or adsorption methods well known to those familiar with the art and described in the patent and scientific literature (see, for instance, Immunochemistry of Solid-Phase Immunoassay, John E. Butler, CRC Press, 1991 and Immobilized Enzymes, Antigens, Antibodies, and Peptides, edited by Howard H. Weetall, Marcel Dekker, Inc. New York, 1975).

The particles themselves are typically spherical (i.e., "beads or microspheres"), with either a rough or a smooth surface, and are prepared as known in the art. They are made various materials, usually non-porous glass, polystyrene, latex or other polymeric materials, and are generally 0.05 micron to 90 micron diameter, preferably 0.5 to 10 micron in diameter, with densities ranging from about 1 to 2 g/mL, preferably close to the density of water.

The particle/allergen combinations are preferably stored in a buffered solution containing a protein stabilizer and a bacteriostatic agent, for use as desired.

Once the subsets of individual allergen/particles combinations are prepared, the subsets can be used individually or can be mixed together to form a single assemblage of allergens coupled to particles. This may be done either in advance of conducting assays, so as to provide a preassembled panel of allergens for use in general, or may be done for each individual assay, for instance, in case it is desired to tailor one or more assays to the geographical location or environment of certain patients. Particle concentrations can be determined and adjusted using a conventional counter and the desired number of particles for the assay can be aliquoted. It is preferred that the number of particles in suspension be of limited quantity and in a limited volume to insure assay sensitivity, speed and adaptability to automated microassay formats (if an automated assay is to be used). The particles in suspension should be at a density close to that of water and suspended in a buffered or aqueous medium sufficient in volume to allow molecular motion and molecular contact and to be adaptable to microassay formats.

The panel for testing can contain, overall, as few as 2, preferably as few as about 5, and up to about 100, specific allergens or mixtures of allergens; however, panels of 10 to 40 allergens are more common. It is preferred that for each test, the sample is added to a suspension containing from about 1000 particles to about 4000 particles of each set of particle-coupled allergen or mixture of allergens, preferably in a small volume, for example, a volume of from about 1 to about 50 µL, preferably from about 5-25 µL. Thus, for example, a test with a panel of 10 allergens would contain about 10,000 particles in 5-20 microliters of a buffered solution. Likewise a test with a panel of 20 allergens would incorporate about 20,000 particles in a 5-20 microliter volume. Increasing the number of particles in an assay decreases the amount of time required to identify and read the particles.

The particles thus prepared are contacted with an individual's blood sample. The blood sample will have a volume of from about 1 to about 25 µL, preferably from about 1 to about 10 µL, and most preferably from about 1 to about 5 µL. Those familiar with the art will recognize that binding of analytes to antigens or antibodies is influenced by incubation conditions such as time, temperature, pH, ionic strength of reagents, and the like, and the conditions of a given assay will be chosen as known in the art to optimize the sensitivity and specificity of the test and generally suit the ease of use of the protocol and its adaptability to automation. In general, such conditions include a temperature of from about 18 to about 37° C., preferably ambient temperatures of from about 18 to about 25° C., and a time of from about 15 minutes to about 24 hours, preferably 1 hour or less. During the first incubation phase, specific antibodies from an individual's blood sample will bind to specific allergens on particles through normal antigen-antibody binding forces. The suspension will contain both free specific and free non-specific antibodies as well as particle-bound specific antibodies.

For the determination of total immunoglobulin antibodies in a sample of blood, anti-human antibody coupled to particles are contacted with an individual's sample. The sample will have a volume of from about 0.5 to about 10 µL, preferably from about 1 to about 5 µL, most preferably from about 1 to about 2 µL. Incubation times and conditions are determined as described herein. In one embodiment of this invention, the test for total immunoglobins is capable of determining levels up to 4800 ng/mL total immunoglobins.

Then, a first conjugate comprising an antibody to the specific analyte, such as anti-human IgE, that is coupled to the first member of a specific binding pair is sequentially added to the mixture. Separation of the solid phase particles from the reaction medium and sample is not required. The specific binding pair is a pair of molecules that have binding specificity for one another. Examples of types of specific binding pairs are biotin-avidin, biotin-streptavidin, digoxin-antidigoxin, and complementary homopolynucleotides poly (dA)-poly (dT) (described in U.S. Pat. No. 6,245,513). The biotin-streptavidin specific binding pair is a preferred embodiment of this invention. In a preferred embodiment a plurality of one member of the specific binding pair (e.g., biotin) is coupled (conjugated) to the antibody (e.g., anti-human IgE). The second member of the specific binding pair, e.g., streptavidin, is coupled to a fluorescent label or fluorophore moiety, as described below. The binding of the second specific binding pair member, streptavidin, to the plurality of biotins conjugated to antibody, amplifies the fluorescent signal, providing greater assay sensitivity. Biotinylation of antibody can be carried out by techniques well known in the art. Typically, antibody-biotin conjugates either obtained commercially or prepared contain 5 to 10 biotin molecules per antibody molecule. In this preferred application, optimum assay sensitivity is obtained when from about 10 to about 30 biotin molecules are coupled per antibody molecule, preferably, about 15-25 biotin molecules per antibody molecule.

Here again, those familiar with the art will recognize that binding of analytes to antigens or antibodies is influenced by incubation conditions such as time, temperature, pH, ionic strength of reagents, and the like, and the conditions of a given assay will be chosen as known in the art to optimize the sensitivity and specificity of the test and generally suit the ease of use of the protocol and its adaptability to automation. In general, such conditions include a temperature of from about 18 to about 37° C., preferably ambient temperatures of from about 18 to about 25° C., and a time of from about 15 minutes to about 24 hours, preferably 1 hour or less. During the second incubation phase, secondary binding agents will bind to the analyte-particle complex through normal antigen-antibody binding forces.

Selection of the conjugates is done with an objective of enhancing assay performance and sensitivity through a $10^{-9}$ to $10^{-12}$ molar range without encountering fluorescent quenching and hook effects.

After a suitable incubation period of the first conjugate with the particle and sample mixture, a second conjugate, containing the second member of the specific binding pair conjugated to a fluorophore, is added to the mixture. The second binding pair member is preferably avidin or streptavidin, most preferably streptavidin, though, as mentioned above, it may be anti-digoxin or materials described in U.S. Pat. No. 6,245,513. Covalent attachment of fluorescent labels to avidin or streptavidin may be effected by a variety of techniques previously described in patent and scientific literature (Haugland, R. P., Bhalagat, M. K., Preparation of avidin conjugates, Methods Mol. Biol. 1998; 80:185-96). Typical fluorescent moieties are described in Chapter 3 of the Manual of Clinical Laboratory Immunology, supra. Alternatively the conjugates may be obtained from a commercial sources. Fluorescent dyes such as fluorescein, the arylsulfonate cyanine dyes, phycobiliprotein dyes, bodipy dyes and the like, may be used. If the particle subsets are distinguished from one another on the basis of incorporation of fluorochromes, the dyes used in the conjugates are selected so as to have fluorescent emissions that are distinct from, and do not interfere with, the emission spectra of the particle subsets. A preferred type of fluorescent material is a class of compounds known as phycobiliproteins, more particularly the phycoerytherins, the phycocyanins, and the allophycocyanins, most preferably the phycoerytherins. Phycoerytherin conjugates have sensitivities ranging from five to ten times greater than that of corresponding fluorescein conjugates, with quantum yields of up to 0.98 and extinction coefficients of up to 2.4 million ($cm^{-1}$ $M^{-1}$). Most preferred of these is R-phycoerytherin. In the second conjugate, the molecular ratio of fluorescent dye to second binding pair member generally can range from about 1:1 to up to about greater than 5:10 with molecular weights ranging from about 300,000 to 3,000,000 or more daltons. The preferred molecular weight of the second conjugate generally is about 400,000 to about 1,000,000 daltons.

The materials are incubated under appropriate conditions for binding of the binding pair members. These, as are known in the art, typically include a temperature of from about 18° C. to about 45° C., preferably from about 18° C. to about 25° C. and a time of from about 15 minutes to about 24 hours, preferably from about 15 minutes to about 3 hours.

In this overall process, the fluorescently labeled antibodies bind to the particles through the first and second binding partners, and through the binding of antibody to analyte antigen. They thus can be detected and measured by application of excitation energy having a wavelength selected to excite the chosen fluorescent label, where the emission spectra that is generated is distinct from the emission spectra incorporated in the particles.

An important feature of the overall method of this invention is that the immunoassay can be conducted without sample dilution. Furthermore, by enabling the use of small volume samples, a homogeneous assay format with solid phase particles, with appropriate assay range and sensitivity, is now possible.

In one embodiment of this invention, applicable to both specific and total immunoglobin assays, the individual who submitted the sample, or another individual acting with his or her permission, can obtain access to the test results over the Internet, or a similar global computer system, for instance, from a Web site via a Web server.

As used herein, the term "Web server" may also refer to a plurality of servers organized to handle a large number of requests for a Web server, i.e., a distributed Web server system. The term "Web site" is often used to refer to a collection of Web servers organized by a business entity or other entity for their purposes. A user is said to "go to" or "access" a Web site when the user directs his or her Web client to make a request of one or the site's Web servers and display the response to the user (even though the user and the Web client do not actually move physically). The user perception is that there is a location on the Web where this Web site exists, but it should be understood that the term "Web site" often refers to the Web server or servers that respond to requests from Web clients, even though "site" does not necessarily refer to the physical location of the Web servers. In fact, in many cases, the servers that serve up a Web site might be distributed physically to avoid downtime when local outages of power or network service occur.

The term "Web site" typically refers to a collection of pages maintained by a common maintainer for presentation to visitors, whether the collection is maintained on one physical server at one physical location or is distributed over many locations and/or servers. The pages (or the data/program code needed to generate the pages dynamically) need not be created by the common maintainer of the collection of pages. Such a maintainer of the collection of pages is typically referred to as the Web site operator.

The term "Web site" also includes Web sites connected to the Web clients via an intranet, wireless access protocol (WAP) network, a local area network (LAN), a wide area network (WAN), a virtual private network (VPN) or another network arrangement. "Web" typically refers to "World Wide Web" (or just "the WWW"), a name given to the collection of hyperlinked documents accessible over the Internet using HTTP. As used herein, "Web" might refer to the World Wide Web, a subset of the World Wide Web, a local collection of hyperlinked pages, or the like.

In this embodiment of the invention, the submitter of the sample (or someone else having authorization from the submitter, such as a relative, physician or other care provider) can obtain access to information respecting the test results, on a Web site, Web "page" or the like. A Web page typically consists of certain information. Web pages include both static pages and dynamic pages. Static pages are pages that are stored on the server, or in storage accessible by the server, prior to the request and are sent from storage to the client in response to a request for that page. Dynamic pages are pages that are generated, in whole or in part, upon receipt of a request. For example, where the page is a view of data from a database, a server might generate the page dynamically using rules or templates and data from the database where the particular data used depends on the particular request made.

The submitter can be assigned a password or code (PIN) that permits access to his or her test results on a web page or within a database that is maintained by, or for, the testing organization (e.g. testing laboratory). Thus, in this embodiment a submitter may also receive the test results without having to visit a physician's office, and may then provide such information to a physician of his or her choice, at his or her convenience.

Computer software that may be used to maintain, and provide access to, such test results, is available from vendors, and does not form a part of this invention.

The following assay procedure was used for all the examples described herein.

a. Extracted allergens, typically from trees, grasses, molds, foods, danders and the like, are coupled to microparticles by covalent or adsorbed procedures. Each allergens extract is coupled to a unique subset of particles, with each subset distinguishable by an incorporated fluorescent emissions or particle size where such differing characteristics can be recognized by appropriate instrumentation. The allergen-coupled particle subsets are stored individually or the subsets are combined as a panel of allergens in a buffered medium with protein stabilizers and bacteriostatic agents. To determine specific IgE levels to a panel of 10 allergens, for example, 10 μL of the combined particle subsets, totaling 10,000 particles, each allergen particle subset represented by 1,000 particles, are placed in a microfuge tube or microtiter well. For total immunoglobulin determinations, anti-human IgE is coupled to microparticles by covalent or adsorbed procedures, and 1,000 particles are placed in a microfuge tube or microtiter well for each test.

b. Blood, plasma or serum collected from an individual by means of the fingerstick collection kit as described herein, or other collection methods, is appropriately labeled or bar coded for identification. A few drops of collected blood, plasma or serum is adequate for determining specific antibody levels to a panel of allergens. A 5 µL sample is added to the allergen-coupled particles residing in the microfuge tubes or microtiter wells. The combined mixture can be briefly vortexed (with microfuge tubes) or shaken (microtiter plate shaker) and incubated for 1 hour at room temperature. For total immunoglobulin determinations, a 1 µL sample is added to the anti-human IgE coupled particles residing in the microfuge tube or microtiter well for each test.

c. Then, a volume of an antibody-biotin conjugate, as described, in a buffered solution, is added to the sample and the allergen-coupled particle mixture described above. The total material is then briefly vortexed or shaken again and allowed to incubate for 1 hour at ambient temperature.

d. A volume of a streptavidin-R-phycoerytherin conjugate, as described, in a buffered solution, is then added to the mixture (c), and the resulting mixture is again briefly vortexed or shaken and allowed to incubate for 1 hour at ambient temperature.

Following this incubation, the resulting mixture of materials is subjected to a reading via appropriate flow cytometric instrumentation, such as the Luminex Corporation Luminex 100 System® or the Becton-Dickinson Immunosytometry FACSCAN® instruments, which simultaneously determines the particle subset by the particle incorporated fluorescent emissions or particle size and measures the emission spectra of the R-phycoerytherin attached to the particle via antigen-antibody and biotin-streptavidin binding as previously described. To determine quantitative concentration levels of specific antibody to allergens, known standards, traceable to the World Health Organization standard (e.g., WHO IgE Standard 75/502 IU/mL), are run to provide a standard curve, from which the concentration of specific IgE in a patient's sample for each allergen is extrapolated, recorded and reported. Specific levels of antibody to allergens can be reported in concentration units, as for example, Units per milliliter and/or class levels, as those acquainted with in vitro allergy diagnostics will recognize.

The following are illustrative examples of the invention.
Preparation of Biotinylated Antibodies:
Biotinylated Anti-Human IgE:

To 15 µL of biotin (biotin amidocaproate N-hydroxysuccinimide ester) (Sigma, MO USA) 25 mg/mL in Dimethylformamide (Sigma) is added 0.4 mL of affinity purified anti-human IgE (Bethy Labs, TX, USA) 3.0 mg/mL in 0.1M $NaHCO_3$. The reagent solution is stirred for 1 hour at 25° C. Hyroxylamine (Spectrum Quality Products, CA, USA), 20 µL, 20 mg/mL in 0.1M $NaHCO_3$ is added and the solution briefly mixed. The biotinylated antibody solution is purified on a Sephadex G-25 (Pharmacia, Sweden) desalting column equilibrated with Phosphate Buffered Saline (PBS), pH 7.2, containing 0.1% Sodium Azide (Sigma)

Covalent Coupling of Allergens to Particles—General Procedure

Carboxylated polystyrene microspheres (Luminex Corporation, TX, USA) are suspended in 80 µL of 0.1M MES Buffer (Fisher Scientific, PA, USA) pH 6.1. To the suspension is added 10 µL of N-Hydroxysulfosuccinimide sodium salt (Pierce Chemicals, IL, USA) 50 mg/mL and 10 µL of 1-(3-dimethylaminopropyl)-3-Ethyl-carbodiimide hydrochloride (Pierce Chemicals, IL, USA) 5 mg/mL. The solution is vortexed and let stand in the dark for 15-20 minutes at ambient temperature. The activated microspheres are centrifuged for 5 minutes at 5000 g and the supernatant is aspirated. The microspheres are then resuspended in 250 µL of 0.1M PBS solution (0.1 M Sodium Phosphate, 0.14 M NaCl) pH 7.3. The mixture is vortexed, the activated microspheres centrifuged and the supernatant aspirated as before.

The activated microspheres are then resuspended in 250 µL of allergen extract, purified proteins or recombinant proteins. Then the mixture is rotated (protected from light) for at least 1 hour at ambient temperature and centrifuged for 5 minutes at 5000 g. The supernatant is aspirated and the microspheres resuspended in 250 µL of PBS/HSA Buffer pH 7.3, containing 0.01 M PBS and 0.02 mg/mL Human Serum Albumin (Sigma, MO, USA), and vortexed to wash the microspheres of residual allergen extract. The supernatant is again centrifuged and aspirated as previously described. The wash procedure is repeated two more times and the microspheres resuspended in 250 µL PBS/HSA. Microsphere concentrations in solution is determined by counting using a hemocytometer (Fisher Scientific, PA, USA) and microscope (Nippon Kogaku, Japan).

Example 1

Assay for Specific IgE Levels to Allergens

Subsets of fluorescently labeled microspheres obtained from Luminex Corporation were covalently coupled with Alternaria mold, Bermuda grass, Timothy grass, Cat dander, Mountain Cedar tree, Egg white, Milk, Wheat, Ragweed and Mite extracted proteins. Serum samples obtained from atopic and non-atopic individuals were assayed against this panel of ten allergens. A 5 µL sample was added to 10 µL of suspended allergen-coupled microspheres placed in V-bottom polypropylene microtiter wells (Evergreen Scientific, CA, USA) or 0.5 mL polypropylene microfuge tubes (Evergreen Scientific, CA, USA). For the six point standard curve, 5 µL of serum standards (secondary standards calibrated against the WHO IgE Standard 75/502) were each added to 10 µL of antigen-coated microspheres in microtiter wells. The microtiter plate was placed on a microtiter plate shaker (Fisher Scientific, PA, USA) and shaken for 10-20 seconds. Microspheres with standards or sample were incubated for 1 hour at room temperature as described above. A 40 µL volume of anti-human IgE-biotin conjugate was added directly to the contents in each well; the plate was briefly shaken as before and the contents incubated for 1 hour at ambient temperature. Subsequently, a 40 µL volume of streptavidin-R-phycoerytherin conjugate (Advanced Biosystems, CA, USA) was added to the contents of each well and incubated for 1 hour at ambient temperature. The microspheres were then directly introduced to the Luminex 100 Flow cytometer for aspiration into the instrument which simultaneously identifies the emission signals of the subset particles and the presence of the R-phycoerytherin fluorescent label residing on the particles. The standard curve was determined using a four parameter Lorentizian cumulative non-linear transition function equation and levels of specific IgE to allergens interpolated from the standard curve as shown in FIG. 1.

FIG. 1 shows the results from two non-allergic and three allergic individuals with positive specific IgE responses to a panel of ten allergens. A 5 µL volume of sample from each individual was used in a three-hour homogeneous assay procedure to simultaneously measure specific IgE levels to the ten allergens coupled to microspheres. Measurement of fluorescent intensity signals using the Luminex 100 System was used to report the results in either IU/mL or class units as interpolated from a six-point standard curve from 0.35 IU/mL. Response interpretations range from Negative to Extremely High based on class levels obtained.

Example 2

Total IgE Assay

Goat anti-human IgE (B ethyl Laboratories, TX, USA) was coupled to microsphere particles (Luminex Corporation, TX, USA) following the same procedure described above for coupling allergens. Serum samples were obtained from individuals obtained by the methods described above. A 1.0 µL volume of standard (secondary standards calibrated against the WHO IgE Standard 75/502) or individual sample was added to 25 µL of suspended microspheres coupled with antibody in microtiter wells, briefly shaken as described above and incubated for 1 hour. A 40 µL volume of anti-human IgE-biotin conjugate was subsequently added to the contents of each well and incubated for 1 hour. Subsequently, a 40 µL volume of streptavidin-Riphycoerytherin conjugate was added to the contents of each well, the microtiter plate briefly shaken and the mixture incubated for 1 hour. The microspheres were then directly introduced to the Luminex 100 Flow cytometer for aspiration into the instrument which simultaneously identifies the emission signals of the subset particles and the presence of the R-phycoerytherin fluorescent label residing on the particles. The standard curve was determined using a four parameter Lorentizian cumulative non-linear transition function equation and levels of total IgE in the samples interpolated from the standard curve as shown in FIG. 2.

Figure 2:
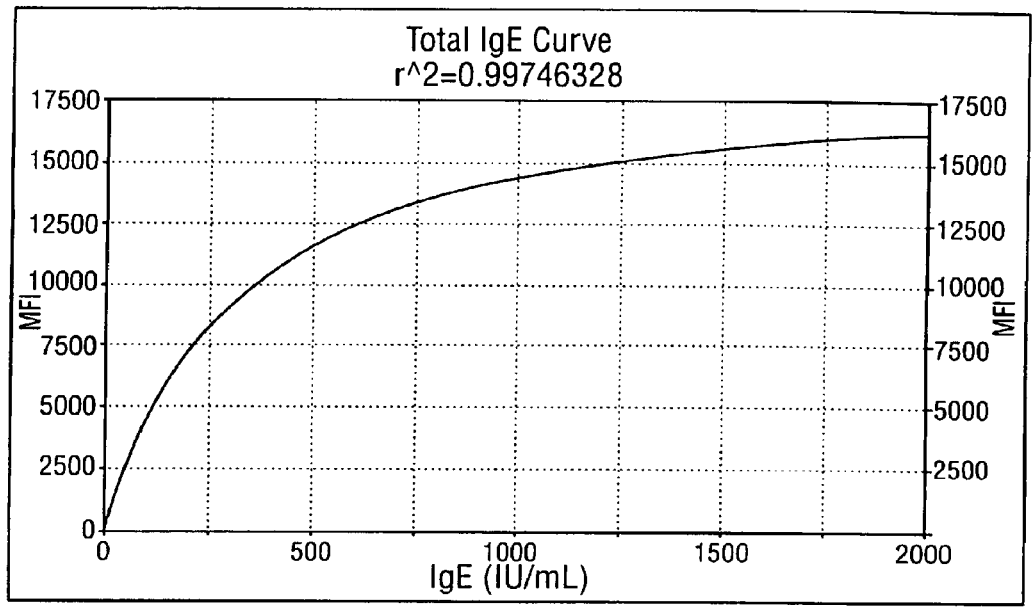
FIG. 2 is a tabulated and graphical view of a total IgE assay in accordance with Example 2.

FIG. 2 shows the results of the Total IgE Standard Curve and Total IgE results of ten individuals. A 1 µL volume of sample from each individual was used in a three-hour homogeneous assay procedure. The amount of total IgE bound to anti-human IgE-coupled microspheres was determined by measuring the signal intensity from the fluorescent reporter signals using the Luminex 100 System and interpolated from a six-point standard curve from 2-2000 IU/mL. Expected results on samples were provided by a reference laboratory using an alternative essay procedure.

We claim:

1. A system for a homogeneous immunoassay testing for an allergic response in a patient, comprising:
    a response mixture having an undiluted serum sample component from the patient with labeled subsets of specific allergen-coupled particles under conditions that enable binding of the allergen-coupled particles to allergen-specific IgE antibodies from the patient's serum sample;
    a first binding agent component for adding to the response mixture, the first binding agent comprising an anti-human IgE antibody covalently bound to a first member of a binding pair;
    a labeled second binding agent for adding to the response mixture containing the first binding agent, the labeled second binding agent comprising a second member of the binding pair and a label, wherein the second member of the binding pair has an affinity for binding to the first member of the binding pair;
    an apparatus component for determining the amounts of the allergen-specific antibodies from the serum sample that are bound to specific allergens by (i) identifying and distinguishing the labeled particles to identify the subsets of specific allergens and (ii) measuring the amount of labeled second binding agent in each of the subsets of allergens;
    wherein, the first binding agent and the second binding agent are preselected to enable detection of anti-human IgE antibodies at a detection sensitivity ranging from about $10^{-9}$ g/ml to about $10^{-12}$ g/ml, and the undiluted serum is limited to having a volume of about 0.5 µL to about 25 µL;
    wherein, the molecular ratio of anti-human antibody to the first member of the binding pair in the first binding agent is from about 1:10 to about 1:30, the second binding agent has a molecular weight of between about 400,000 and about 1,000,000 Daltons, and the selection of the first binding agent, the second binding agent, and serum volume has the function of avoiding quenching of a signal from the label of the labeled second binding agent and high dose hook effects;
    and wherein, the detection sensitivity ranging from $10^{-9}$ g/ml to $10^{-12}$ g/ml is measured under homogeneous assay conditions.

2. The system of claim 1, wherein the labeled particles are fluorescently labeled microspheres, and the undiluted serum sample ranges in volume from about 1.0 µL to about 10 µL.

3. The system of claim 1, wherein the first binding agent comprises an anti-human IgE-biotin conjugate having about 15-25 biotin molecules per antibody molecule, the second binding agent comprises a streptavidin-phycoerytherin conjugate, and the mole ratio of the first binding agent to the second binding agent ranges from about 1:1 to about 1:5.

4. The system of claim 1, wherein the labeled particles enable identification of subsets of allergens, and the subsets compose a panel of allergens having from about 2 specific allergens to about 100 specific allergens.

5. The system of claim 1, wherein the system further comprises a kit having a device for puncturing the skin and obtaining a blood sample, and a container for holding and transmitting the blood sample to a laboratory for extracting the serum sample and measuring the allergic response of the patient to an allergen or panel of allergens.

6. The system of claim 1, wherein the system further comprises a computer network component having testing results for the patient on a non-transitory computer readable storage medium accessible by the patient to obtain testing results.

7. The system of claim 1, wherein the first binding agent comprises an anti-human IgE-digoxin conjugate.

8. The system of claim 1, further comprising a flow cytometer.

9. A system for a homogeneous immunoassay testing for an allergic response in a patient, comprising:
    a response mixture having an undiluted serum sample component from the patient with labeled subsets of specific allergen-coupled particles under conditions that enable binding of the allergen-coupled particles to allergen-specific antibodies from the patient's serum sample;
    a first binding agent component for adding to the response mixture, the first binding agent comprising an anti-human antibody covalently bound to a first member of a binding pair;
    a labeled second binding agent for adding to the response mixture containing the first binding agent, the labeled second binding agent comprising a second member of the binding pair and a label, wherein the second member of the binding pair has an affinity for binding to the first member of the binding pair;

an apparatus component for determining the amounts of the allergen-specific antibodies from the serum sample that are bound to specific allergens by (i) identifying and distinguishing the labeled particles to identify the subsets of specific allergens and (ii) measuring the amount of labeled second binding agent in each of the subsets of allergens;

wherein, the first binding agent and the second binding agent are preselected to enable detection of anti-human antibodies at a detection sensitivity ranging from about $10^{-9}$ g/ml to about $10^{-12}$ g/ml, and the undiluted serum is limited to having a volume of about 0.5 µL to about 25 µL;

wherein, the molecular ratio of anti-human antibody to the first member of the binding pair in the first binding agent is from about 1:10 to about 1:30, the second binding agent has a molecular weight of between about 400,000 and about 1,000,000 Daltons, and the selection of the first binding agent, the second binding agent, and serum volume has the function of avoiding quenching of a signal from the label of the labeled second binding agent and high dose hook effects;

and wherein, the detection sensitivity ranging from $10^{-9}$ g/ml to $10^{-12}$ g/ml is measured under homogeneous assay conditions.

10. The system of claim 9, wherein the labeled particles are fluorescently labeled microspheres, and the undiluted serum sample ranges in volume from about 1.0 µL to about 10 µL.

11. The system of claim 9, wherein the first binding agent comprises an anti-human antibody-biotin conjugate having about 15-25 biotin molecules per antibody molecule, the second binding agent comprises a streptavidin-phycoerytherin conjugate, and the mole ratio of the first binding agent to the second binding agent ranges from about 1:1 to about 1:5.

12. The system of claim 9, wherein the labeled particles enable identification of subsets of allergens, and the subsets compose a panel of allergens having from about 2 specific allergens to about 100 specific allergens.

13. The system of claim 9, wherein the system further comprises a kit having a device for puncturing the skin and obtaining a blood sample, and a container for holding and transmitting the blood sample to a laboratory for extracting the serum sample and measuring the allergic response of the patient to an allergen or panel of allergens.

14. The system of claim 9, wherein the system further comprises a computer network component having testing results for the patient on a non-transitory computer readable storage medium accessible by the patient to obtain testing results.

15. The system of claim 9, wherein the first binding agent comprises an anti-human antibody-digoxin conjugate.

16. The system of claim 9, wherein the allergen-specific antibodies from the patient's serum sample are allergen-specific IgG antibodies, and the anti-human antibody in the first binding agent is an anti-human IgG antibody.

17. The system of claim 9, further comprising a flow cytometer.

18. A system for a homogeneous immunoassay testing for an allergic response in a patient, comprising:

a response mixture having an undiluted serum sample component from the patient with labeled subsets of specific allergen-coupled particles under conditions that enable binding of the allergen-coupled particles to allergen-specific IgG antibodies from the patient's serum sample;

a first binding agent component for adding to the response mixture, the first binding agent comprising an anti-human IgG antibody covalently bound to a first member of a binding pair;

a labeled second binding agent for adding to the response mixture containing the first binding agent, the labeled second binding agent comprising a second member of the binding pair and a label, wherein the second member of the binding pair has an affinity for binding to the first member of the binding pair;

an apparatus component for determining the amounts of the allergen-specific antibodies from the serum sample that are bound to specific allergens by (i) identifying and distinguishing the labeled particles to identify the subsets of specific allergens and (ii) measuring the amount of labeled second binding agent in each of the subsets of allergens;

wherein, the first binding agent and the second binding agent are preselected to enable detection of anti-human IgG antibodies at a detection sensitivity ranging from about $10^{-9}$ g/ml to about $10^{-12}$ g/ml, and the undiluted serum is limited to having a volume of about 0.5 µL to about 25 µL;

wherein, the molecular ratio of anti-human antibody to the first member of the binding pair in the first binding agent is from about 1:10 to about 1:30, the second binding agent has a molecular weight of between about 400,000 and about 1,000,000 Daltons, and the selection of the first binding agent, the second binding agent, and serum volume has the function of avoiding quenching of a signal from the label of the labeled second binding agent and high dose hook effects;

and wherein, the detection sensitivity ranging from $10^{-9}$ g/ml to $10^{-12}$ g/ml is measured under homogeneous assay conditions.

19. The system of claim 18, wherein the labeled particles are fluorescently labeled microspheres, and the undiluted serum sample ranges in volume from about 1.0 µL to about 10 µL.

20. The system of claim 18, wherein the first binding agent comprises an anti-human IgG-biotin conjugate having about 15-25 biotin molecules per antibody molecule, the second binding agent comprises a streptavidin-phycoerytherin conjugate, and the mole ratio of the first binding agent to the second binding agent ranges from about 1:1 to about 1:5.

21. The system of claim 18, wherein the labeled particles enable identification of subsets of allergens, and the subsets compose a panel of allergens having from about 2 specific allergens to about 100 specific allergens.

22. The system of claim 18, wherein the system further comprises a kit having a device for puncturing the skin and obtaining a blood sample, and a container for holding and transmitting the blood sample to a laboratory for extracting the serum sample and measuring the allergic response of the patient to an allergen or panel of allergens.

23. The system of claim 18, wherein the system further comprises a computer network component having testing results for the patient on a non-transitory computer readable storage medium accessible by the patient to obtain testing results.

24. The system of claim 18, wherein the first binding agent comprises an anti-human IgG-digoxin conjugate.

25. The system of claim 18, further comprising a flow cytometer.

* * * * *